United States Patent
Qian et al.

(10) Patent No.: US 7,547,446 B2
(45) Date of Patent: Jun. 16, 2009

(54) DRY HEMOSTATIC COMPOSITIONS AND METHODS FOR THEIR PREPARATION

(75) Inventors: Zhen Qian, Fremont, CA (US); A. Edward Osawa, San Francisco, CA (US); Cary J. Reich, Los Gatos, CA (US)

(73) Assignees: Baxter International, Inc., Deerfield, IL (US); Baxter Healthcare S.A., Zurich (CH)

( * ) Notice: Subject to any disclaimer, the term of this patent is extended or adjusted under 35 U.S.C. 154(b) by 0 days.

(21) Appl. No.: 11/766,516

(22) Filed: Jun. 21, 2007

(65) Prior Publication Data

US 2007/0248685 A1    Oct. 25, 2007

Related U.S. Application Data

(62) Division of application No. 09/908,464, filed on Jul. 17, 2001, now Pat. No. 7,435,425.

(51) Int. Cl.
*A61K 13/00* (2006.01)
*A61F 2/00* (2006.01)
*A61K 9/14* (2006.01)
*A61K 9/50* (2006.01)
*A61K 9/16* (2006.01)

(52) U.S. Cl. ............... 424/422; 424/423; 424/489; 424/491; 424/492; 424/499

(58) Field of Classification Search .......... None
See application file for complete search history.

(56) References Cited

U.S. PATENT DOCUMENTS

| 2,507,244 | A | | 5/1950 | Correll |
| 2,558,395 | A | | 6/1951 | Studer |
| 4,292,972 | A | | 10/1981 | Pawelchak et al. |
| 4,540,410 | A | | 9/1985 | Wood et al. |
| 4,543,332 | A | | 9/1985 | Jao et al. |
| 5,908,054 | A | | 6/1999 | Safabash et al. |
| 6,063,061 | A | * | 5/2000 | Wallace et al. ............ 604/181 |
| 6,066,325 | A | | 5/2000 | Wallace et al. |
| 6,458,386 | B1 | * | 10/2002 | Schacht et al. ............ 424/488 |

OTHER PUBLICATIONS

Hood et al., "Efficacy of Topical Hemostat Floseal Matrix in Vascular Surgery," 24th World Congress of the International Society for Cardiovascular Surgery (Sep. 12-16, 1999), 2 pages total.

* cited by examiner

*Primary Examiner*—Humera N. Sheikh
(74) *Attorney, Agent, or Firm*—Townsend and Townsend and Crew LLP

(57) ABSTRACT

Dry cross-linked gelatin compositions are prepared that rapidly re-hydrate to produce gelatin hydrogels suitable as hemostatic sealants. Gelatin is cross-linked in the presence of certain re-hydration aids, such as polyethylene glycol, polyvinylprovidone, and dextran, in order to produce a dry cross-linked gelatin powder. The use of the re-hydration aids has been found to substantially increase the re-hydration rate in the presence of an aqueous re-hydration medium, typically thrombin-containing saline.

17 Claims, 1 Drawing Sheet

DRY HEMOSTATIC COMPOSITIONS AND METHODS FOR THEIR PREPARATION

CROSS REFERENCES TO RELATED APPLICATIONS

This application is a divisional of U.S. patent application Ser. No. 09/908,464 filed Jul. 17, 2001, now U.S. Pat. No. 7,435,425 the entire contents of which are incorporated herein by reference for all purposes.

BACKGROUND OF THE INVENTION

1. Field of the Invention

The present invention relates generally to collagen and collagen-derived compositions and methods for their preparation. In particular, the present invention relates to a method for producing a dry cross-linked gelatin or other collagen or collagen-derived composition which is capable of absorbing water at an enhanced rate.

Fusion Medical Technologies, Inc., assignee of the present application, produces a hemostatic composition under the FloSeal® trade name. The FloSeal® product is available in a package including two syringes. A first syringe is filled with granules of cross-linked bovine gelatin which are pre-hydrated with a buffer solution. The gelatin hydrogel contains about 85% (w/w) water and is in the form of a flowable hydrogel. Immediately prior to use in the operating room, thrombin in aqueous saline is mixed with the gelatin hydrogel. The thrombin is prepared in saline and drawn up in a second syringe, and the syringes are connected together permitting mixing of thrombin and the gelatin.

The resulting mixture of the gelatin hydrogel granules and the thrombin has been found to be a highly effective hemostatic sealant when applied to a bleeding site. Typically, the sealant will be applied through the syringe in which it has been mixed to the bleeding site. Blood will percolate through the resulting bed of hydrogel granules, and the thrombin reacts with fibrinogen in the blood to form a fibrin clot around the gelatin to seal the bleeding site.

Although highly effective, the present FloSeal® product has a limited shelf life. It is believed that the stability of the gelatin is reduced by hydrolysis of the packaged hydrogel. To limit possible hydrolytic degradation, the FloSeal® product is usually shipped in a temperature-protected packaging.

For these reasons, it would be desirable to provide improved hemostatic sealing compositions of the type which combine a collagen, gelatin, or other collagen-derived hydrogel with a thrombin-containing aqueous solution. In particular, it would be desirable to provide such compositions in a form which would be resistant to hydrolytic degradation and which would therefore have a longer shelf life. It would be particularly desirable to provide improved compositions having both comparable hemostatic activity to the present FloSeal® product and longer shelf lives. Such compositions would be most beneficial if they could be rapidly re-hydrated for subsequent use, typically so that they could be extruded through a syringe. At least some of these objectives will be met by the inventions described hereinafter.

2. Description of the Background Art

The FloSeal® product available from Fusion Medical Technologies, Inc., is described in Hood et al., *Efficacy of Topical Hemostat FloSeal™ in Vascular Surgery*, an Abstract funded by Fusion Medical Technologies, Inc., which was publicly presented in September 1999. Patents covering the FloSeal® product include U.S. Pat. Nos. 6,063,061 and 6,066,325. A dual syringe system suitable for mixing and delivering a collagen, gelatin, or other collagen-derived component and a thrombin component of the FloSeal™ product is described in U.S. Pat. No. 5,908,054. The complete disclosures of each of these patent references is hereby incorporated by reference.

BRIEF SUMMARY OF THE INVENTION

The present invention provides improved hemostatic sealing compositions, methods for preparing such improved compositions, and kits comprising the improved compositions. The methods and compositions will be particularly useful for providing hemostasis at bleeding sites, including surgical bleeding sites, traumatic bleeding sites and the like. An exemplary use of the compositions may be in sealing the tissue tract above a blood vessel penetration created for vascular catheterization.

The compositions comprise a dry cross-linked gelatin powder which has been prepared to re-hydrate rapidly. The gelatin powder preferably comprises relatively large particles, also referred to as fragments or sub-units, as described in U.S. Pat. Nos. 6,063,061 and 6,066,325, the full disclosures of which have previously been incorporated by reference. A preferred particle size will be the range from 150 µm to 750 µm, but particle sizes outside of this preferred range may find use in many circumstances. The dry compositions will also display a significant "equilibrium swell" when exposed to an aqueous re-hydrating medium. Preferably, the swell will be in the range from 400% to 1000%, but may fall outside of this range as set forth in the above-referenced patents. "Equilibrium swell" may be determined by subtracting the dry weight of the gelatin hydrogel powder from its weight when fully hydrated and thus fully swelled. The difference is then divided by the dry weight and multiplied by 100 to give the measure of swelling. The dry weight should be measured after exposure of the material to an elevated temperature for a time sufficient to remove substantially all residual moisture, e.g., two hours at 120° C. The equilibrium hydration of the material can be achieved by immersing the dry material in a suitable re-hydrating medium, such as aqueous saline, for a time period sufficient for the water content to become constant, typically for from 18 to 24 hours at room temperature.

The dry cross-linked gelatin powders of present invention will usually have some residual moisture, but will be sufficiently dry to achieve the desired stability and extended shelf life. Typically, the dry compositions will have a moisture content below 20% by weight (w/w) or less, preferably having a moisture content in the range from 5% by weight to 15% by weight. To maintain dryness, the compositions will typically be packaged in a manner suitable to prevent moisture incursion, as described in more detail in connection with the kits of the present invention.

In one particular aspect of the present invention, compositions will comprise cross-linked gelatin powders having a moisture content of 20% (w/w) or less, wherein the powder was cross-linked in the presence of a re-hydration aid so that the powder has an aqueous re-hydration rate which is at least 5% higher than the re-hydration rate of a similar powder prepared without the re-hydration aid. The "re-hydration rate" is defined herein to mean the quantity of an aqueous solution, typically 0.9% (w/w) saline, that is absorbed by a gram of the powder (dry weight basis) within thirty seconds, expressed as gm/gm. Particular techniques for measuring this rate are described in the Experimental section hereinafter. Preferred compositions of the present invention will have a re-hydration rate of at least 3 gm/gm, preferably at least 3.5 gm/gm, and often 3.75 gm/gm or higher. Re-hydration rates of similar powders prepared without the re-hydration aids are typically below three, and a percentage increase in re-hydration rate will usually be at least 5%, preferably being at least 10%, and more preferably being at least 25% or higher.

The dry cross-linked gelatin powders of the present invention having improved re-hydration rates are preferably obtained by preparing the powders in the presence of certain re-hydration aids. Such re-hydration aids will be present during the preparation of the powders, but will usually be removed from the final products. For example, re-hydration aids which are present at about 20% of the total solids content, will typically be reduced to below 1% in the final product, often below 0.5% by weight. Exemplary re-hydration aids include polyethylene glycol (PEG), preferably having a molecular weight of about 1000; polyvinylpyrrolidone (PVP), preferably having an average molecular weight of about 50,000; and dextran, typically having an average molecular weight of about 40,000. It is preferred to employ at least two of these re-hydration aids when preparing the compositions of the present invention, and more particularly preferred to employ all three.

The methods of the present invention thus comprise providing an aqueous solution of a non-cross-linked gelatin combined with a re-hydration aid. The non-cross-linked gelatin will typically be present in an aqueous solution at from 5% (w/w) to 15% (w/w) and the re-hydration aids will be typically present from 5% to 30% (w/w) based on the weight of gelatin in the aqueous solution. Preferably, the re-hydration aid comprises PEG at from 2.5% to 20% (w/w) based on the weight of the gelatin, PVP at from 1.25% to 20% (w/w), and dextran at from 1.25% to 20% (w/w).

The non-cross-linked gelatin together with the re-hydration aid is then cross-linked in any manner suitable to form the hydrogel. For example, polymeric molecules may be cross-linked using bi- or poly-functional cross-linking agents which covalently attach to two or more polymer molecules chains. Exemplary bifunctional cross-linking agents include aldehydes, epoxies, succinimides, carbodiimides, maleimides, azides, carbonates, isocyanates, divinyl sulfone, alcohols, amines, imidates, anhydrides, halides, silanes, diazoacetate, aziridines, and the like. Alternatively, cross-linking may be achieved by using oxidizers and other agents, such as periodates, which activate side-chains or moieties on the polymer so that they may react with other side-chains or moieties to form the cross-linking bonds. An additional method of cross-linking comprises exposing the polymers to radiation, such as gamma radiation, to activate the polymer chains to permit cross-linking reactions. Dehydrothermal cross-linking methods may also be suitable. Preferred methods for cross-linking gelatin molecules are described below.

Exemplary methods for producing cross-linked gelatins are as follows. Gelatin is obtained and suspended in an aqueous solution to form a non-cross-linked hydrogel, typically having a solids content from 1% to 70% by weight, usually from 3% to 10% by weight. The gelatin is cross-linked, typically by exposure to either glutaraldehyde (e.g., 0.01% to 0.05% w/w, overnight at 0 C. to 15 C in aqueous buffer), sodium periodate (e.g., 0.05 M, held at 0° C. to 15° C. for 48 hours) or 1-ethyl-3-(3-dimethylaminopropyl)carbodiimide ("EDC") (e.g., 0.5% to 1.5% w/w overnight at room temperature), or by exposure to about 0.3 to 3 megarads of gamma or electron beam radiation. Alternatively, gelatin particles can be suspended in an alcohol, preferably methyl alcohol or ethyl alcohol, at a solids content of 1% to 70% by weight, usually 3% to 10% by weight, and cross-linked by exposure to a cross-linking agent, typically glutaraldehyde (e.g., 0.01% to 0.1% w/w, overnight at room temperature). In the case of aldehydes, the pH should be held from about 6 to 11, preferably from 7 to 10. When cross-linking with glutaraldehyde, the cross-links are formed via Schiff bases which may be stabilized by subsequent reduction, e.g., by treatment with sodium borohydride. After cross-linking, the resulting granules may be washed in water and optionally rinsed in an alcohol, and dried. The resulting dry powders may then be loaded into the applicators of the present invention, as described in more detail hereinafter.

After cross-linking, at least 50% (w/w) of the re-hydration aid will be removed from the resulting hydrogel. Usually, the re-hydration aid is removed by filtration of the hydrogel followed by washing of the resulting filter cake. Such filtration/washing steps can be repeated one or more additional times in order to clean the product to a desired level and to remove at least 50% of the re-hydration aid, preferably removing at least 90% (w/w) of the re-hydration aid originally present.

After filtration, the gelatin is dried, typically by drying the final filter cake which was produced. The dried filter cake may then be broken up or ground to produce the cross-linked powder having a particle size in the desired ranges set forth above.

Kits according to the present invention will comprise a first container holding the dry cross-linked gelatin powder of the present invention, as described above. The kits will further comprise a second container holding an aqueous re-hydration medium, typically a saline or other aqueous solution comprising thrombin which is intended to be mixed with the gelatin as the gelatin is re-hydrated. The containers can be in any form, but will preferably be in the form of syringes which permit mixing of the dry gelatin with the re-hydration medium.

DESCRIPTION OF THE SPECIFIC EMBODIMENTS

Figure 1:
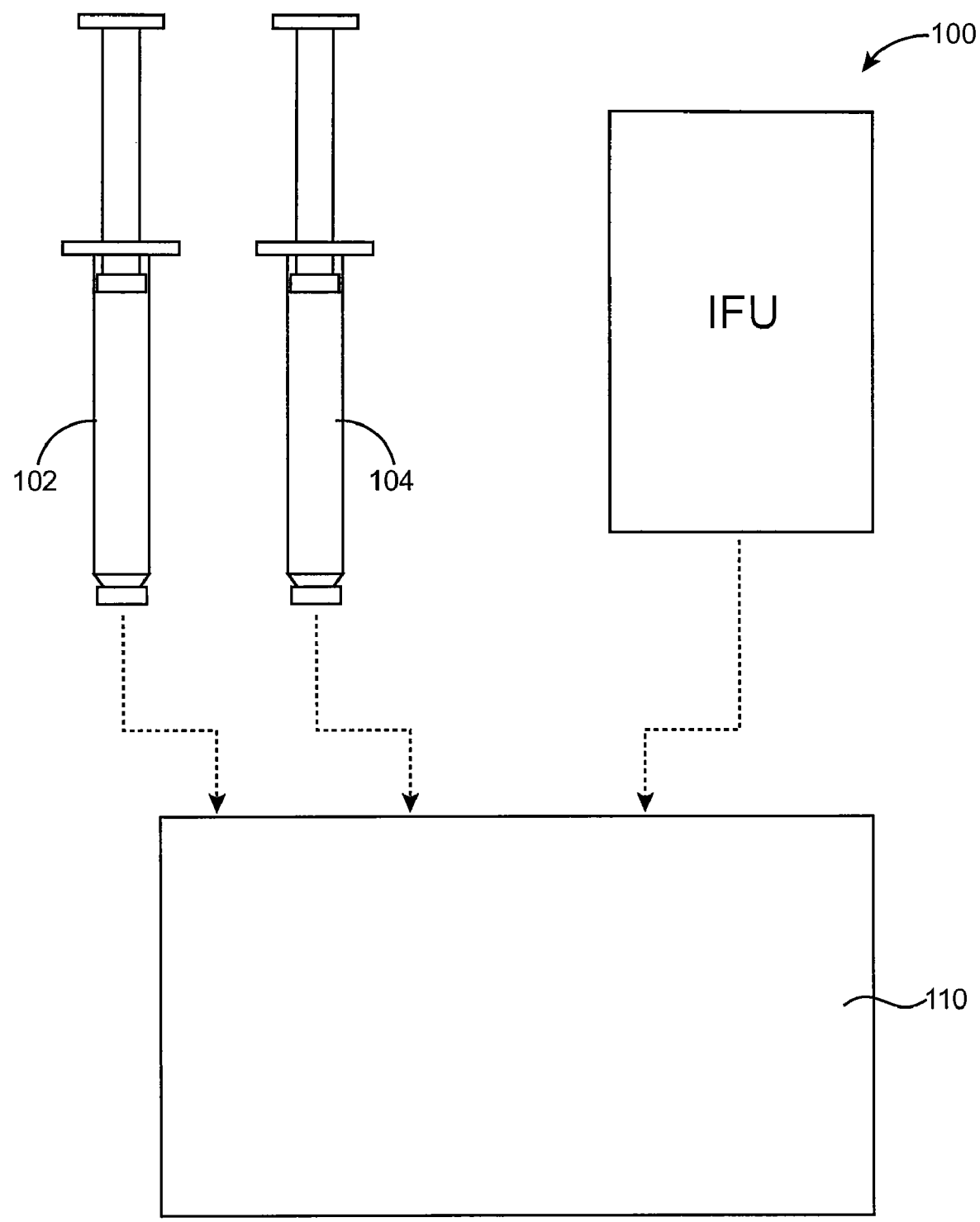
FIG. 1 illustrates a kit constructed in accordance with the principles of the present invention.

The following examples are offered by way of illustration, not by way of limitation.

EXAMPLE 1

Preparation of Gelatin Powder

Strips of bovine corium were suspended in a sodium hydroxide solution of concentration 1 M to 2 M for 1 hr at room temperature, neutralized with phosphoric acid, and rinsed. The treated strips were then resuspended in deionized water, adjusted to pH 7-8, and heated to 70° C. A homogenizer was used to further reduce the size of the strips. After 1 hr at 70° C., the corium was largely solubilized to gelatin. The amount of corium was chosen so that the solids content of the resulting gelatin solution was approximately 3-10% (w/w), typically 7-10%. The solution was cast as thin layers onto Teflon® coated metal trays, dried, and ground to form gelatin powder.

EXAMPLE 2

Preparation of "Modified Gelatin Powder"

Re-hydration aids (Table 1) were dissolved in 500 mL of 50° C. de-ionized water and then an amount of bovine derived gelatin powder, prepared as in Example 1, was added to the solution. The final concentration of gelatin in solution was chosen to be approximately 8% (w/w, bulk gelatin powder basis), and the total amount of re-hydration aids in the solution was chosen as in Examples 9-44 (Tables 1 and 2). After the gelatin had dissolved, the solution was poured into Teflon® coated metal trays and dried. The dried gelatin sheet is ground to form "modified gelatin powder".

Alternatively, strips of bovine corium were suspended in a sodium hydroxide solution of concentration 1 M to 2 M for 1 hr at room temperature, neutralized with phosphoric acid, and rinsed. The treated strips were then resuspended in deionized water, adjusted to pH 7-8, and heated to 70° C. A homogenizer was used to further reduce the size of the strips. After 1 hr at 70° C., the corium was largely solubilized to gelatin. The amount of corium was chosen so that the solids content of the resulting gelatin solution was approximately 3-10% (w/w), typically 7-10%. Amounts of re-hydration aids were chosen as in Examples 9-44 (Tables 1 and 2) and were then added to the gelatin solution, either in solid form or dissolved in a small volume of water. The solution was cast into thin layers onto Teflon® coated metal trays, dried, and ground to form "modified gelatin powder". Examples of several formulations for modified gelatin are given in Tables 1 and 2.

EXAMPLE 3

Preparation of Cross-linked Gelatin Powder from "Modified Gelatin Powder"

600 mL of 0.2 M phosphate buffer (pH 9.2±0.2) was cooled to a temperature below 12° C. 0.32 mL of glutaraldehyde (25%) was added to the buffer solution and then 20 g of modified gelatin powder was added, resulting in a glutaraldehyde concentration of 4000 ppm (glutaraldehyde to modified gelatin, bulk weight basis). The gelatin was suspended in the glutaraldehyde solution with a stir bar. The pH of each suspensions was adjusted to a range of 9.2±0.2 and then maintained at a temperature of 9 to 12° C. and pH of 9.2±0.2 over 19 hours.

The suspension was filtered and the filter cake was washed with de-ionized water three times by completely covering the filter cake with de-ionized water and then allowing the vacuum to draw the rinse water through the cake. The filter cake was left in the funnel during each rinse.

0.2 g of NaBH4 was dissolved in 600 mL 25 mM phosphate buffer, pH 7.4 0.2, in a beaker. The above filter cake was suspended in the NaBH4 solution at room temperature (about 22° C.) for 3 hours, then filtered to remove the liquid.

The filter cake was next suspended in 600 mL of buffer solution at room temperature (about 22° C.) for 30 minutes and filtered again. The buffer was composed of sodium phosphate (dibasic anhydrous and monobasic monohydrate) and sodium ascorbate. The above procedure was repeated twice to ensure that the appropriate ratio of salts to gelatin were present to form the desired buffer composition upon reconstitution. The filter cake was dried, then ground with a Waring Blender, resulting in "cross-linked gelatin powder".

This method was also used to prepare cross-linked gelatin powder from unmodified gelatin powder; that is, gelatin to which no re-hydration aids were added during its preparation.

EXAMPLE 4

Preparation of Irradiated Product from Cross-Linked Gelatin Powder

About 800 mg (bulk weight) of the cross-linked gelatin powder, prepared as in Example 2, were put into each of several 5 cc syringes. The syringes containing powder were sterilized with gamma irradiation at ambient temperature.

EXAMPLE 5

Use of Product as a Hemostatic Agent

A syringe of product containing approximately 0.8 g of irradiated cross-linked gelatin powder was prepared from modified gelatin powder. The modified gelatin powder was prepared as in Example 2. The modified gelatin was further cross-linked and irradiated as in Examples 3 and 4. The product was mixed with 4 mL of a saline solution containing about 1000 Units of bovine thrombin per milliliter. Mixing was achieved by passage back and forth between two syringes connected with a female-female straight-through Luer connector. The powder in the syringe was hydrated as it mixed with the thrombin solution, forming granules of hydrogel.

A square lesion, approximately 1 cm×1 cm×0.2 cm deep, was created on the liver of a farm-grade pig. The pig had been anticoagulated with heparin so that its activated clotting time (ACT) was three to five times its baseline value, and the lesion bled freely prior to treatment. After about 30 seconds from the start of mixing, approximately 2 mL of the hydrated powder was extruded from the syringe onto the lesion and held in place with compression for two minutes. After compression was removed, the treated lesion was observed for bleeding at 3 min, 10 min, and 50 min after application. No bleeding was seen from the treated lesion at the 3 min and 10 min observation. After the 10 min observation, the treated lesion was irrigated with saline solution. While excess material was removed, no re-bleeding was observed. At 50 min after application, the lesion was observed again and no bleeding was seen.

EXAMPLE 6

Determination of Re-hydration Rate of a Powder

The "re-hydration rate" of a powder was measured as follows. The powder, packed in a 5 cc syringe, was mixed with a syringe containing a volume of aqueous solution by passage between the two syringes connected with a Luer fitting for 30 seconds. The volume of aqueous solution was chosen to be in excess of what could be expected to be absorbed in 30 seconds. Typically, 0.8 g (bulk weight) of powder was mixed with 3 mL of 0.9% sodium chloride solution. The resulting mixture was then immediately filtered to remove any unabsorbed liquid. The wet filtered material was weighed, then dried in a 120° C. oven for two hours and re-weighed. This measurement gave the total amount of water removed from the wet material and the weight of the dry powder. The amount of water that had been absorbed by the powder was then calculated after a small correction is made for the residual moisture that had been present in the powder originally. The "re-hydration rate" was given as the mass of saline solution absorbed per gram dry weight of powder in that 30 second interval.

In the calculation below, the fraction solids of the bulk powder ("S") was measured independently by drying the bulk powder at 120° C. for 2 hr and weighing the powder before and after drying. The value of S is given by the following:

$$S = \frac{\text{weight after drying at } 120°\text{C., 2 hr}}{\text{weight before drying}}$$

Re-hydration rate calculation:
A: initial weight of the pan and filter paper
B: weight of the pan, filter paper and hydrated powder
C: weight of the pan, filter paper and sample after drying in oven
S: fraction solids of the bulk powder originally in syringe
M: grams of saline absorbed per gram of powder (dry weight) during mixing ("absorption rate")

$$M = \frac{(B-A) - (C-A)/S}{(C-A)}$$

EXAMPLE 7

Re-hydration Rate and Physical Property Determination for Several Batches of Powder Product Tables 1 and 2 depict the results of re-hydration rate measurements performed on one to for several batches of powder product (Examples 9-23). These were made using methods as per Examples 1, 2, 3, and 4. Except for Examples 9 and 17, these were prepared from modified gelatins that were made with various proportions of gelatin and the following re-hydration aids: polyethylene glycol (PEG), average molecular weight 1000; polyvinylpyrrolidone (PVP), "k-30" designation, corresponding to an average molecular weight of about 50,000; and dextran, average molecular weight 40,000.

It is seen that use of several different combinations of gelatin and re-hydration aids can result in a powder product that absorbs more aqueous saline solution in 30 seconds per gram of powder than powder product made from gelatin to which no re-hydration aids have been added. It is also seen that the combination of gelatin, PEG, PVP and dextran at a bulk weight ratio of 80:10:5:5 in the modified gelatin (Example 10) produces a powder product that absorbs about 33% more saline solution per gram in 30 seconds than powder product made from unmodified gelatin.

Table 1 also gives values for other physical properties determined for the powder product lots. "Percent solids" was determined by weighing the powder before and after drying at 120° C. for two hours to drive off residual moisture. "DSC peak temperature" refers to the temperature at which a peak is exhibited in a thermogram of a differential scanning calorimetry measurement conducted from 1° C. to 70° C. "Equilibrium swell" was determined by suspending the powder in an excess of saline solution for at least 18 hr at room temperature. The hydrated powder was weighed to determine its "equilibrium wet weight" and dried at 120° C. for two hours and re-weighed to determine its "dry weight". Equilibrium swell is given as $$\text{Equilibrium swell (\%)} = 100\% \times \frac{\text{equilibrium wet weight} - \text{dry weight}}{\text{dry weight}}$$

Values for "mean particle size" were measured by light scattering in a Coulter LS particle size analyzer.

From the data presented in Table 1, it appears that the appropriate use of re-hydration aids can change the re-hydration rate of the powder product without significantly changing other physical properties.

EXAMPLE 8

Measurement of Polyethylene Glycol, Polyvinylpyrrolidone, and Dextran Levels in Modified Gelatin Powder and in Cross-Linked Powder Approximately 50 mg modified gelatin or 250 mg cross-linked irradiated powder product were suspended in 10 mL of deionized water and heated for 3 hr at 65° C. The samples were then centrifuged at 15 minutes at 2000 rpm. The resulting supernatant was filtered through a 0.45 μm Gelman Acrodisc filter, the first mL being discarded. The resulting sample was then assayed by three different high performance liquid chromatography (HPLC) methods to quantitate the polyethylene glycol (PEG), polyvinylpyrrolidone (PVP), and dextran in the sample. For PEG, 100 μL of the sample was injected onto a Waters Ultrahydrogel 120 column, 7.8×300 mm, with guard column and prefilter, using deionized water as the mobile phase. A refractive index detector was used to monitor the effluent. For PVP, 100 μL of the sample was injected onto a Phenomenex Kingsorb C18 5 μm column, 4.6×150 mm, with guard column and prefilter, using a gradient of methanol and aqueous sodium phosphate as the mobile phase. An ultraviolet absorbance detector was used to monitor the effluent. For dextran, 100 μL of the sample was injected onto a Waters Ultrahydrogel Linear column, 7.8×300 mm, with guard column and prefilter, using 0.1 M sodium phosphate, pH 7 and acetonitrile at a 90:10 ratio as the mobile phase. A refractive index detector was used to monitor the effluent. All columns were heated to 40° C. for the analyses. The limit of quantitation was about 0.1% (w/w sample) for PEG and PVP, 0.2% (w/w sample) for dextran.

Modified gelatin was prepared as per Example 2. The modified gelatin was analyzed for PEG, PVP and dextran in the manner described above. Results indicated that PEG, PVP, and dextran were present at 16%, 8%, and 3% (w/w bulk) respectively. The modified gelatin was subsequently subjected to cross-linking, sodium borohydride treatment, and rinsing as per Example 3 to form cross-linked modified gelatin powder. When this powder was analyzed for PEG, PVP, and dextran by HPLC in the manner described above, the content of each of the three re-hydration aids was found to be below the limit of quantitation.

EXAMPLE 9

Powder Product Made Without Re-hydration Aids

Unmodified gelatin—that is, gelatin to which processing aids were not added—was prepared from bovine corium strips as in Example 1 and cross-linked as in Example 3. The cross-linked unmodified gelatin was then packed into syringes and gamma irradiated as in Example 4. Physical properties of the resulting product were measured as in Examples 6 and 7 and are given in Table 1.

EXAMPLES 10-23

Powder Product Made With Re-hydration Aids

Batches of modified gelatin were prepared as in Example 2 from gelatin powder or corium strips and from one, two, or three re-hydration aids. Table 1 gives the proportions of bulk gelatin and re-hydration aids used. The modified gelatin was then cross-linked as in Example 3. Except for Example 17, the re-hydration aids used were from the following list: polyethylene glycol (PEG) of an average molecular weight of about 1000; polyvinylpyrrolidone (PVP), "k-30" designation, of an average molecular weight of about 50,000; and dextran, of an average molecular weight of about 40,000. In Example 17, PEG of an average molecular weight of about 400 was used. The cross-linked modified gelatin was then packed into syringes and gamma irradiated as in Example 4. Physical properties of the resulting powder product from each of these preparations were measured as in Examples 6 and 7 and are given in Table 1. Data given with the formulation for Example 10 is the average and standard deviation of nine batches prepared according to that formulation.

EXAMPLES 24-44

Powder Product Made With Various Re-Hydration Aids

Batches of modified gelatin were prepared as in Example 2 from gelatin powder or corium strips and from one of several re-hydration aids. Table 2 gives the identity and concentration of re-hydration aid used in each batch as a ratio of bulk gelatin weight to re-hydration aid and as a percentage of total bulk solute used to prepare the modified gelatin. The modified gelatin was then cross-linked as in Example 3. The cross-linked modified gelatin was then packed into syringes and gamma irradiated as in Example 4. Physical properties of the resulting powder product from each of these preparations were measured as in Examples 6 and 7 and are given in Table 2. Data for the Example 9 formulation is provided in Table 2 for comparison.

TABLE 1

| | | Target bulk weight percent in modified gelatin | | | | Properties of powder product after cross-linking and gamma irradiation (re-hydration aids largely removed) | | | |
|---|---|---|---|---|---|---|---|---|---|
| Lot | | Gelatin (bulk weight) | PEG MW = 1000 D | PVP MW ~50000 D | Dextran MW = 40000 D | % solids | DSC peak temp (° C.) | Equilibrium swell (%) | Mean particle size (μm) | Re-hydration* |

| Lot | | Gelatin | PEG | PVP | Dextran | % solids | DSC | Swell | Size | Re-hyd |
|---|---|---|---|---|---|---|---|---|---|---|
| *No re-hydration aids added* | | | | | | | | | | |
| Example 9 | 208-32 | 100 | 0 | 0 | 0 | 88.6 | 41.3 | 551 | 440 | 2.85 |
| Preferred composition (four-way mixture) | | | | | | | | | | |
| Example 10 | avg of 9 lots | 80 | 10 | 5 | 5 | 87.6 | 42.1 | 595 | 423 | 3.79 |
| | std. deviation of 9 lots | | | | | 1.0 | 1.4 | 43 | 65 | 0.15 |
| *Three-way mixtures* | | | | | | | | | | |
| Example 11 | 228-69-1 | 80 | 10 | 10 | 0 | 88.1 | 40.8 | 667 | 387 | 3.51 |
| Example 12 | 228-69-2 | 80 | 10 | 0 | 10 | 88.4 | 40.6 | 670 | 367 | 3.14 |
| Example 13 | 228-78 | 80 | 0 | 10 | 10 | 86.7 | 41.1 | 632 | 414 | 3.20 |
| *Gelatin-PEG mixtures* | | | | | | | | | | |
| Example 14 | 212-39-2 | 94 | 6 | 0 | 0 | 86.2 | 44.4 | 502 | 372 | 2.68 |
| Example 15 | 228-42-3 | 89 | 11 | 0 | 0 | 88.6 | 42.8 | 594 | 428 | 3.16 |
| Example 16 | 228-42-1 | 80 | 20 | 0 | 0 | 88.9 | 42.4 | 575 | 312 | 3.47 |
| Example 17 | 214-62-1 | 89 | 11** | 0 | 0 | 87.1 | 40.7 | 599 | 406 | 3.11 |
| *Gelatin-PVP mixtures* | | | | | | | | | | |
| Example 18 | 228-38-3 | 94 | 0 | 6 | 0 | 88.2 | 42.2 | 567 | 399 | 3.26 |
| Example 19 | 228-38-2 | 89 | 0 | 11 | 0 | 88.3 | 41.0 | 605 | 422 | 3.44 |
| Example 20 | 228-38-1 | 80 | 0 | 20 | 0 | 88.6 | 42.4 | 596 | 401 | 3.52 |
| *Gelatin-dextran mixtures* | | | | | | | | | | |
| Example 21 | 228-35-3 | 94 | 0 | 0 | 6 | 88.1 | 40.5 | 631 | 395 | 3.18 |
| Example 22 | 228-35-2 | 89 | 0 | 0 | 11 | 88.3 | 41.4 | 598 | 345 | 3.03 |
| Example 23 | 228-35-1 | 80 | 0 | 0 | 20 | 88.5 | 41.9 | 624 | 392 | 3.01 |

*Re-hydration rate defined as grams saline absorbed per gram powder product (dry wt) in 30 sec
**PEG (MW = 400) used instead of MW = 1000

TABLE 2

| | Lot | Re-hydration aid type | MW or other designation | bulk gelatin wt: aid | Conc'n of processing aid in modified gelatin (bulk wt %) | % solids | DSC peak temp (° C.) | Equilibrium swell (%) | Mean particle size (μm) | Re-hydration rate* |
|---|---|---|---|---|---|---|---|---|---|---|
| Example 9 | 208-32 | no re-hydration aids | | | | 88.6 | 41.3 | 551 | 440 | 2.85 |
| Example 24 | 214-11-1 | glycerol | n/a | 4 | 20% | 85.5 | 43.4 | 483 | 653 | 2.19 |
| Example 25 | 214-11-2 | glycerol | n/a | 8 | 11% | 86.4 | 43.4 | 529 | 421 | 2.62 |
| Example 26 | 214-11-3 | glycerol | n/a | 16 | 6% | 86.5 | 43.0 | 543 | 398 | 2.35 |
| Example 27 | 214-44-1 | dextran | 148000 D | 4 | 20% | 85.5 | nr | 634 | 433 | 2.62 |
| Example 28 | 214-44-2 | dextran | 148000 D | 8 | 11% | 85.4 | nr | 607 | 453 | 2.57 |
| Example 29 | 214-44-3 | dextran | 148000 D | 16 | 6% | 85.5 | nr | 603 | 527 | 2.33 |
| Example 30 | 214-44-4 | dextran | 148000 D | 32 | 3% | 85.7 | nr | 531 | 491 | 2.37 |
| Example 31 | 228-35-4 | dextran | 40000 D | 32 | 3% | 84.5 | 41.4 | 633 | 380 | 2.59 |
| Example 32 | 214-50-1 | PVP | k-90 | 4 | 20% | 85.3 | 44.0 | 612 | 664 | 2.41 |
| Example 33 | 214-50-2 | PVP | k-90 | 8 | 11% | 85.6 | 44.3 | 538 | 581 | 2.71 |
| Example 34 | 214-50-3 | PVP | k-90 | 16 | 6% | 85.6 | 44.1 | 527 | 593 | 2.78 |
| Example 35 | 214-50-4 | PVP | k-90 | 32 | 3% | 86.1 | 43.0 | 597 | 538 | 2.76 |
| Example 36 | 214-53-4 | PVP | k-30 | 32 | 3% | 87.3 | 41.1 | 580 | 447 | 2.72 |
| Example 37 | 214-59-1 | PEG | 400 | 4 | 20% | 86.7 | 42.0 | 595 | 407 | 2.18 |
| Example 38 | 214-66-1 | PEG | 400 | 6 | 14% | 86.5 | 40.8 | 603 | 501 | 2.63 |
| Example 39 | 212-39-1 | PEG | 400 | 16 | 6% | 86.2 | 43.8 | 513 | 403 | 2.11 |
| Example 40 | 212-39-2 | PEG | 1000 | 16 | 6% | 86.2 | 44.4 | 502 | 372 | 2.68 |
| Example 41 | 214-59-3 | PEG | 8000 | 4 | 20% | 87.4 | 41.5 | 548 | 429 | 2.87 |
| Example 42 | 214-66-3 | PEG | 8000 | 6 | 14% | 86.9 | 41.4 | 581 | 426 | 3.80 |
| Example 43 | 214-62-3 | PEG | 8000 | 8 | 11% | 86.8 | 42.0 | 631 | 511 | 2.78 |
| Example 44 | 212-39-3 | PEG | 8000 | 16 | 6% | 86.4 | 44.6 | 546 | 518 | 2.72 | nr = not reported
*Re-hydration rate defined as grams saline absorbed per gram powder product (dry wt) in 30 sec While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for preparing a substantially dry cross-linked gelatin powder, said method comprising:
   providing an aqueous solution comprising a non-cross-linked gelatin and a re-hydration aid, wherein the rehydration aid in the aqueous solution comprises polyethylene glycol (PEG) in the range from 2.5% (w/w) to 20% (w/w) based on the weight of the gelatin, polyvinylpyrrolidone (PVP) in the range from 1.25% (w/w) to 20% (w/w) based on the weight of the gelatin, and dextran in the range from 1.25% (w/w) to 20% (w/w) based on the weight of the gelatin;
   cross-linking the gelatin in the presence of the re-hydration aid;
   removing at least 50% (w/w) of the re-hydration aid after the cross-linking step; and
   drying the cross-linked gelatin and grinding to produce a powder having a moisture content below 20% (w/w) and a re-hydration rate of at least 3 gm/gm in 30 seconds.

2. A method as in claim 1 wherein cross-linking comprises adding a cross-linking agent to the gelatin solution.

3. A method as in claim 2, wherein the cross-linking agent comprises glutaraldehyde.

4. A method as in claim 1, wherein removing at least 50% of the re-hydration aid comprises filtering the suspension of cross-linked gelatin in a solvent followed by filtration of the gelatin to produce a filter cake and washing the filter cake to remove the re-hydration aid.

5. A method as in claim 4, wherein washing the filter cake removes at least 90% (w/w) of the re-hydration aid originally present in the solution.

6. A method as in claim 4, wherein drying comprises drying the filter cake after washing, wherein the method further comprises breaking up or grinding the dry filter cake to produce the dry ground gelatin powder.

7. A method for preparing a substantially dry cross-linked gelatin powder, said method comprising:
   providing an aqueous solution comprising a non-cross-linked gelatin combined with a re-hydration aid, wherein the rehydration aid in the aqueous solution comprises polyethylene glycol (PEG) in the range from 2.5% (w/w) to 20% (w/w) based on the weight of the gelatin, polyvinylpyrrolidone (PVP) in the range from 1.25% (w/w) to 20% (w/w) based on the weight of the gelatin, and dextran in the range from 1.25% (w/w) to 20% (w/w) based on the weight of the gelatin;
   cross-linking the gelatin in the presence of the re-hydration aid;
   removing at least 50% (w/w) of the re-hydration aid after the cross-linking step; and
   drying the cross-linked gelatin and grinding to produce a powder having a moisture content below 20% (w/w).

8. A method as in claim 7, wherein the powder has a re-hydration rate of at least 3.5 gm/gm.

9. A method as in claim 7, wherein the powder has a re-hydration rate of at least 3.75 gm/gm.

10. A method as in claim 7, wherein the powder has a mean particle size in the range from 150 μm to 750 μm.

11. A method as in claim 7, wherein the powder has an equilibrium swell in the range from 400% to 1000%.

12. A method as in claim 7, wherein the powder has a moisture content in the range from 5% (w/w) to 15% (w/w).

13. A method as in claim 7, wherein the re-hydration aid is present at below 1% of the powder, by weight.

14. A method as in claim 7, wherein the re-hydration aid is present at below 0.5% of the powder, by weight.

15. A method as in claim 7, wherein the non-cross-linked gelatin is present in the aqueous solution in the range from 5% (w/w) to 15% (w/w).

16. A method as in claim 7, wherein the rehydration aid is present in the aqueous solution in the range from 5% (w/w) to 30% (w/w) based on the weight of the non-cross-linked gelatin in the aqueous solution.

17. A method for preparing a substantially dry cross-linked gelatin powder, said method comprising:

providing an aqueous solution comprising a non-cross-linked gelatin combined with a re-hydration aid, wherein the rehydration aid in the aqueous solution comprises polyethylene glycol (PEG) in the range from 2.5% (w/w) to 20% (w/w) based on the weight of the gelatin, polyvinylpyrrolidone (PVP) in the range from 1.25% (w/w) to 20% (w/w) based on the weight of the gelatin, and dextran in the range from 1.25% (w/w) to 20% (w/w) based on the weight of the gelatin;

cross-linking the gelatin in the presence of the re-hydration aid;

removing at least 50% (w/w) of the re-hydration aid after the cross-linking step; and drying the cross-linked gelatin and grinding to produce a powder having a moisture content below 20% (w/w) and a re-hydration rate which is at least 5% higher than a re-hydration rate of a similar powder prepared without the re-hydration aid.

\* \* \* \* \*